United States Patent
Yavus et al.

(10) Patent No.: US 6,292,530 B1
(45) Date of Patent: Sep. 18, 2001

(54) METHOD AND APPARATUS FOR RECONSTRUCTING IMAGE DATA ACQUIRED BY A TOMOSYNTHESIS X-RAY IMAGING SYSTEM

(75) Inventors: Mehmet Yavus, Clifton Park; Peter Michael Edic, Albany; Ahmed Nadeem Ishaque, Clifton Park; Sarah Kathryn Patch, Saratoga Springs, all of NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/360,537

(22) Filed: Jul. 26, 1999

Related U.S. Application Data (60) Provisional application No. 60/131,588, filed on Apr. 29, 1999.

(51) Int. Cl.$^7$ .................................................. A61B 6/02
(52) U.S. Cl. .............................. 378/22; 378/25; 378/901
(58) Field of Search .................................... 378/4, 17, 22, 378/25, 29, 901

(56) References Cited

U.S. PATENT DOCUMENTS

| | | | | |
|---|---|---|---|---|
| 5,020,086 | * | 5/1991 | Peugeot | 378/113 |
| 5,687,209 | * | 11/1997 | Adams | 378/22 |

OTHER PUBLICATIONS

"Tomosynthesis: A Three–Dimensional Radiographic Imaging Technique", by D.G. Grant, IEEE Trans. Biiomed. Eng., vol. BME–19, (Jan. 1972) pp. 20–28.

"Restoration of Digital Multiplate Tomosynthesis by a Constraint Iteration Method", by U. E. Ruttiman et al., IEEE Trans. Med. Img., vol. MI–3(3), (1974) pp. 141–148.

"Elimination of Nonpivotal Palne Images from X–Ray Motion Tomograms", by S. Kawata et al., IEEE Trans. Med. Img., vol. MI–4(3), (Sep. 1985) pp. 153–159.

"Ectomography—A New Radiographic Reconstruction Method—I. Theory and Error Estimates", by H. Knutsson et al., IEEE Trans. Biomed. Eng., vol. BME–27, No. 11, (Nov. 1980) pp. 640–648.

"Three–Dimensional Image Reconstruction by Digital Tomo–Synthesis Using Inverse Filtering", by H. Matsuo et al., IEEE Trans. Med. Img., vol. 12(12) (Jun. 1993) pp. 307–313.

"Practical Cone–Beam Algorithm", by L. Feldkamp et al., J. Opt. Soc. Am., A/vol. 1, No. 6, Jun. 1984.

"A New Cone Beam Reconstruction Algorithm and Its Application to Circular Orbits", by H. Hui, ASL, Tech. Notes, GEMS Milwaukee.

Copending U.S. application No. 09/489,896, filed Jan. 24, 2000, by M. Yavuz, entitled "Method and Apparatus For Performing Tomosynthesis".

Copending U.S. application No. 09/585,786, filed Jun. 5, 2000, by P. Edic et al., entitled "Apparatus, Methods, and Computer Programs For Estimating and Correcting Scatter in Digital Radiographic and Tomographic Imaging".

* cited by examiner

*Primary Examiner*—David V. Bruce
(74) *Attorney, Agent, or Firm*—Donald S. Ingraham; Douglas E. Stoner

(57) ABSTRACT

A method and apparatus are provided which utilize a circular tomosynthesis system to collect 2-D x-ray projection radiograph data of an object being evaluated. The collected data is then transformed into a form suitable for cone beam volumetric computed tomography (cone beam VCT) reconstruction. Once the data has been transformed, a cone beam VCT reconstruction algorithm may be utilized to reconstruct a 3-D image of the object.

27 Claims, 5 Drawing Sheets

METHOD AND APPARATUS FOR RECONSTRUCTING IMAGE DATA ACQUIRED BY A TOMOSYNTHESIS X-RAY IMAGING SYSTEM

CROSS REFERENCE TO RELATED APPLICATIONS

This application claims priority to and the benefit of the filing date of Provisional Application Ser. No. 60/131,588, filed Apr. 29, 1999, entitled "IMAGE RECONSTRUCTION IN CIRCULAR TOMOSYNTHESIS X-RAY IMAGING", which is incorporated herein by reference in its entirety.

BACKGROUND OF THE INVENTION

This invention relates to tomosynthesis and, more particularly, to a method and apparatus that utilizes a tomosynthesis system to acquire 2-D projection images of an object and which then reconstructs a 3-D representation of the object by utilizing a cone beam volumetric computed tomography reconstruction algorithm.

Figure 1:
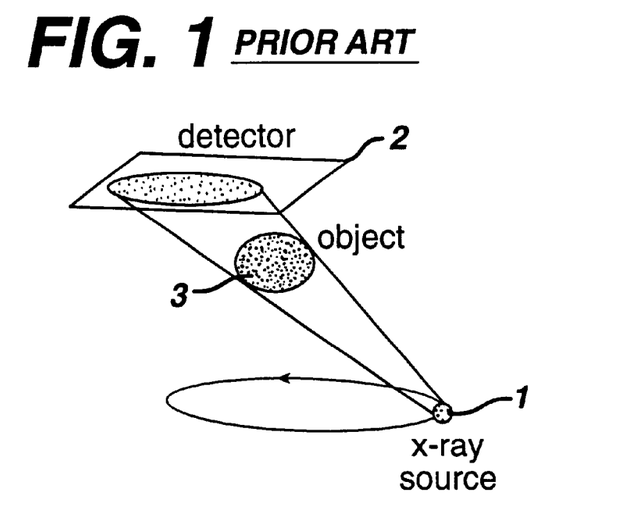
FIG. 1 is an illustration of the system geometry of a typical prior art circular tomosynthesis system.

Circular tomosynthesis enables a three dimensional (3-D) image of an object to be constructed from a finite set of two-dimensional (2-D) projection radiograph images. FIG. 1 illustrates the system geometry of a typical circular tomosynthesis system. The system comprises an x-ray source 1 and a 2-D x-ray detector 2, which is normally a film screen. During data acquisition, both the x-ray source 1 and the detector 2 rotate in circular trajectories and a set of projection radiographs of the object 3 are acquired by the detector 2 at discrete source locations. The circular trajectories are in planes that are parallel to each other and the motions of the source 1 and detector 2 are in opposite directions along the trajectories.

Once the projection radiographs have been obtained, they are then digitized and spatially translated with respect to each other and superimposed in such a manner that the images of structures in the tomosynthesis plane overlap exactly. The images of structures outside the tomosynthesis plane do not overlap exactly, resulting in a depth-dependent blurring of these structures. By varying the amount of relative translation of the projection radiographs, the location of the tomosynthesis plane can be varied. Each time the tomosynthesis plane is varied, the image data corresponding to the overlapping structures is superimposed and a 2-D image of the structure in the tomosynthesis plane is obtained. Once a complete set of 2-D images of the object has been obtained, a 3-D image of the object is generated from the set of 2-D images.

Circular tomosynthesis can be very useful for clinical applications that require high spatial resolution in the direction of coronal slice through the patient, especially since it is usually difficult to obtain high resolution in the coronal slice direction with x-ray computerized tomography (CT). Moreover, the apparatus for tomosynthesis is usually simple and inexpensive compared to x-ray CT. However, one shortcoming of circular tomosynthesis systems is that the image quality of the reconstructed 3-D images usually is limited due to blurring of the structures outside of the tomosynthesis plane. Many reconstruction algorithms have been developed to improve the image quality and to reduce this out-of-plane blurring. For example, algorithms based on matrix inversion techniques have been utilized for this purpose.

Figure 2:
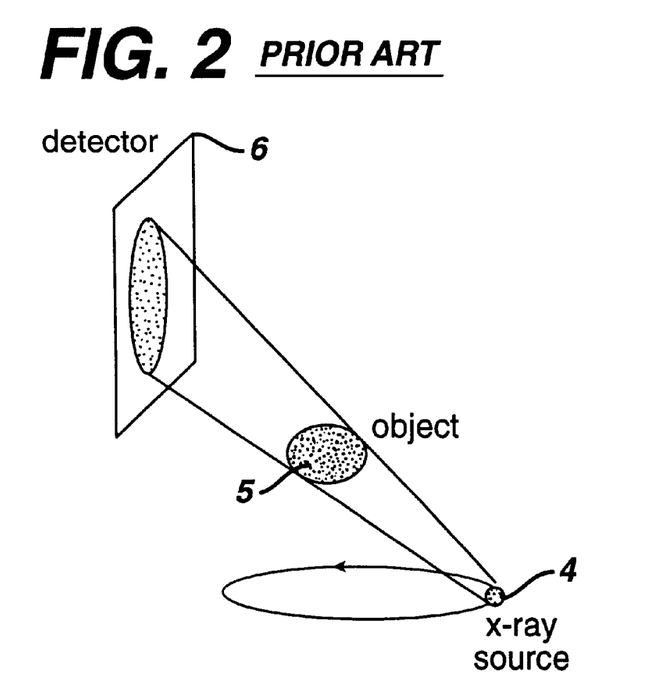
FIG. 2 is an illustration of the system geometry of a typical prior art cone beam volumetric computed tomography (cone beam VCT) system.

A well known technique for generating 3-D reconstructions using 2-D projection images is known as cone beam volumetric computed tomography (cone beam VCT). FIG. 2 illustrates the system geometry of a cone beam VCT system. The x-ray source 4 projects a cone of x-rays onto the object 5. The x-rays impinge on a digital detector 6 which digitizes the data. The detector 6 is in a plane which is not parallel to the plane in which the source 4 is located. Rather, the detector 6 is located in a plane that is orthogonal to the plane in which the source is located.

As with circular tomosynthesis, relative motion is generated between the detector 6/source 4 geometry and the object 5. This can be accomplished by rotating the source 4 and the detector 6 or by rotating the object 5. Images of the object are acquired at certain locations of the source 4 and the detector 6 or at certain locations of the object 5, depending on the manner in which the relative motion is generated. As 2-D maps of the image intensity measured by the detector 6 are generated, these 2-D maps are filtered using known image filtering techniques and are then reconstructed using one or more known algorithms to obtain a 3-D representation of the object.

The 3-D images reconstructed using cone beam VCT systems have higher image quality than the reconstructed images obtained using typical circular tomosynthesis systems. It would be desirable to improve the quality of images obtained using circular tomosynthesis systems, rather than replacing circular tomosynthesis systems with cone beam VCT systems. Replacing circular tomosynthesis systems with cone beam VCT systems may not be an option in many cases due to costs and other factors.

Accordingly, a need exists for a method and apparatus which improves the quality of images reconstructed from image data acquired using circular tomosynthesis systems.

BRIEF SUMMARY OF THE INVENTION

The invention provides a method and apparatus which utilize a circular tomosynthesis system to collect 2-D x-ray projection radiograph data of an object being evaluated. The collected data is then transformed into a form suitable for cone beam volumetric computed tomography (cone beam VCT) reconstruction.

Once the data has been transformed, a cone beam VCT reconstruction algorithm commonly is utilized to reconstruct a 3-D image of the object.

DETAILED DESCRIPTION OF THE INVENTION

Figure 3:
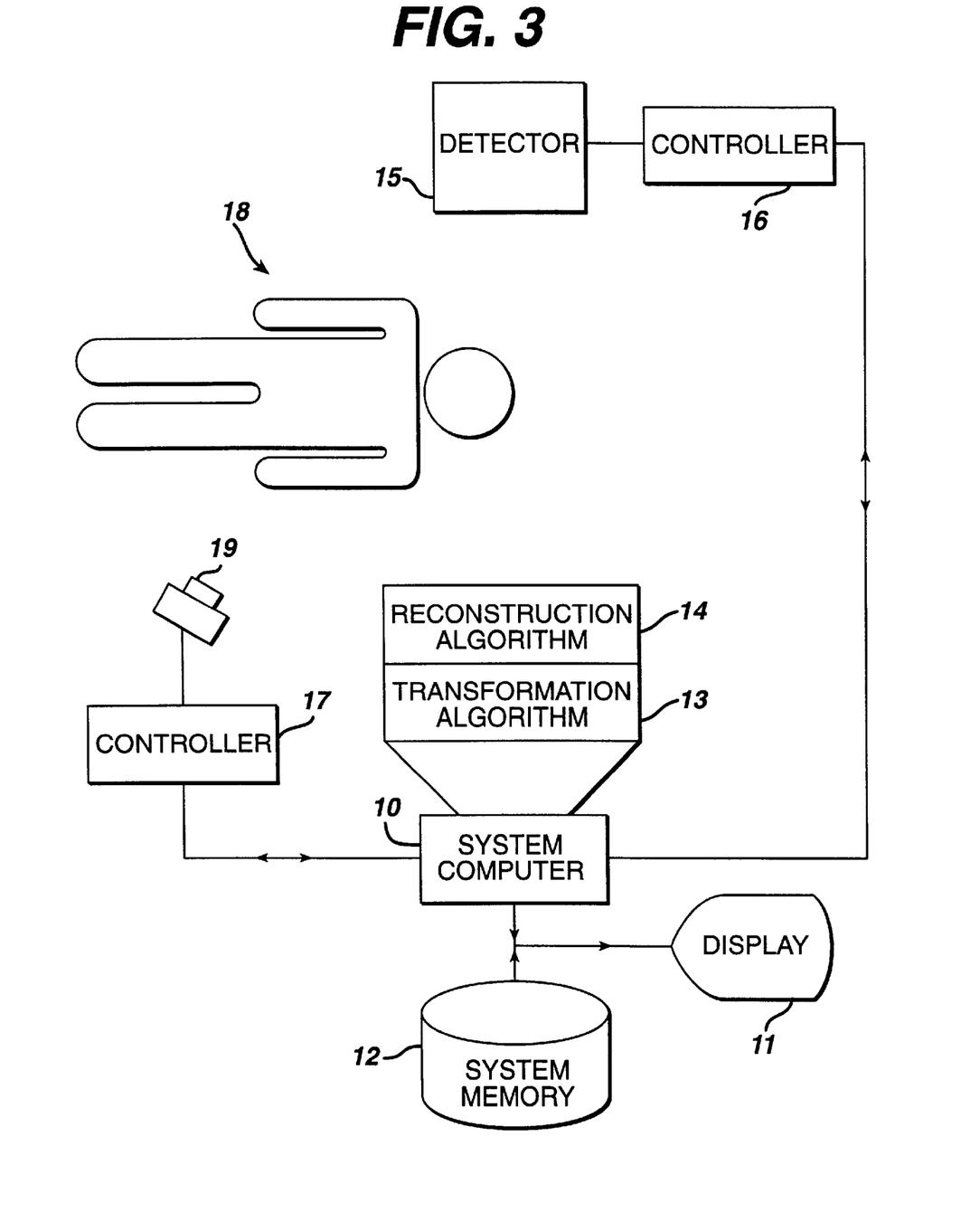
FIG. 3 is a block diagram of the apparatus of the invention in accordance with one embodiment.

FIG. 3 is a block diagram of the apparatus of the invention in accordance with one embodiment of the invention. The apparatus is a circular tomosynthesis system such as that discussed above with reference to FIG. 1. However, in contrast to typical circular tomosynthesis systems, the reconstruction algorithm 14 executed by a logic device 10 is a cone beam VCT reconstruction algorithm. The transformation algorithm 13 executed by the logic device 10 transforms the image data acquired by the circular tomosynthesis system into a form that is suitable for reconstruction by application of the cone beam VCT algorithm 14. The transformation algorithm 13 and the reconstruction algorithm 14 will be discussed below in detail with reference to FIGS. 4 and 5.

The logic device 10 typically comprises a computer that is in communication with a display 11 and with a system data storage component 12. The system data storage component 12 stores data utilized by the computer 10 to perform the. The system data storage component 12 also stores image data which has been acquired by the tomosynthesis system. In addition, the system data storage component 12 stores the code corresponding to the algorithms 13 and 14 and image data which has been reconstructed by application of those algorithms. The system computer 10 is capable of causing reconstructed images to be displayed on the display device 11.

The apparatus of the invention comprises a detector 15, which preferably is a digital detector or image intensifier. The apparatus of the invention comprises an x-ray source 19 for projecting x-rays through the object 18 being imaged, which may be a human patient, for example. The detector 15 receives x-rays that pass through the object 18 and generates voltage signals related to the intensity of the x-rays. The detector 15 and the source 19 are electrically coupled to controllers 16 and 17, respectively. The controllers 16 and 17 are electrically coupled to the computer 10. The computer 10 outputs instructions to the controllers 16 and 17. In response to receiving the instructions from the computer 10, the controllers 16 and 17 move the detector 15 and the source 19 about circular trajectories in the manner described above with reference to FIG. 1.

The manner in which the controllers 16 and 17 generate motion in the detector 15 and source 19 is well known to those skilled in the art. As stated above, the apparatus of the invention preferably utilizes a typical circular tomosynthesis system for acquiring x-ray image data. Therefore, a detailed discussion of the operations of the circular tomosynthesis system and of the data acquisition process will not be provided herein in the interest of brevity.

The instructions received by the controllers 16 and 17 instruct the controllers 16 and 17 as to the manner in which the data acquisition is to be performed. At particular locations of the source 19 along the circular trajectory, image samples are acquired by the detector 15. Detector 15 comprises, for example, a digital detector or image intensifier. Detector 15 typically generates analog voltage signals in response to the x-rays impinging thereon and if the detector 15 is an image intesifier, an analog-to-digital converter (not shown) converts these analog voltage signals into digital voltage signals. The digital voltage signals are then returned to the computer 10 for processing, as described below in detail. acquisition is to be performed. At particular locations of the source 19 along the circular trajectory, image samples are acquired by the detector 15. Detector 15 comprises, for example, a digital database or image intensifier. Detector 15 typically generates analog voltage signals in response to the x-rays impinging thereon and if the detector 15 is an image intensifier, an analog-to-digital converter (not shown) converts these analog voltage signals into digital voltage signals. The digital voltage signals are then returned to the computer 10 for processing, as described below in detail.

It should be noted that rather than moving the detector 15 and source 19, the object being imaged 18 can be moved in order to generate the necessary relative motion between the detector 15, the source 19 and the object 18. Also, those skilled in the art will understand that a variety of mechanisms are available that are suitable for generating motion in the detector 15 and the source 19. Similarly, those skilled in the art will understand that a variety of mechanisms are available that are suitable for generating motion in the object being imaged 18.

Although FIG. 3 illustrates separate controllers 16 and 17 for controlling movement of the detector 15 and source 19, respectively, two controllers are not necessary. A single controller may be used to control the motion of either the detector 15 or source 19, and the detector 15 and source 19 may be mechanically coupled by a linkage mechanism (not shown). The linkage mechanism will maintain synchronization in the motion of the detector 15 and source 19.

It should also be noted that the circular tomosynthesis system invention is not limited to any particular type or configuration . Also, the present invention is not limited to any particular computer for performing the processing tasks of the invention. The term "computer", as that term is used herein, is intended to denote any machine capable of performing the calculations, or computations, necessary to perform the tasks of the invention. The term "computer" is intended to denote any machine that is capable of accepting a structured input and of processing the input in accordance with prescribed rules to produce an output.

The computer 10 comprises a microprocessor (not shown) which performs all of the computing tasks. The system data storage component 12 can be an on-chip or off-chip data storage component, i.e., inside the integrated circuit comprising the microprocessor or external to the integrated circuit. It should be noted that computation devices other than a microprocessor may perform the computations of the invention, such as, for example, an application specific integrated circuit or a digital signal processor.

Furthermore, although the method of the present invention preferably is performed by a combination of hardware and software (i.e., the microprocessor executing the transformation and reconstruction algorithms), it should be noted that the method of the present invention could also be performed solely in hardware, as will be understood by those skilled in the art.

Figure 4:
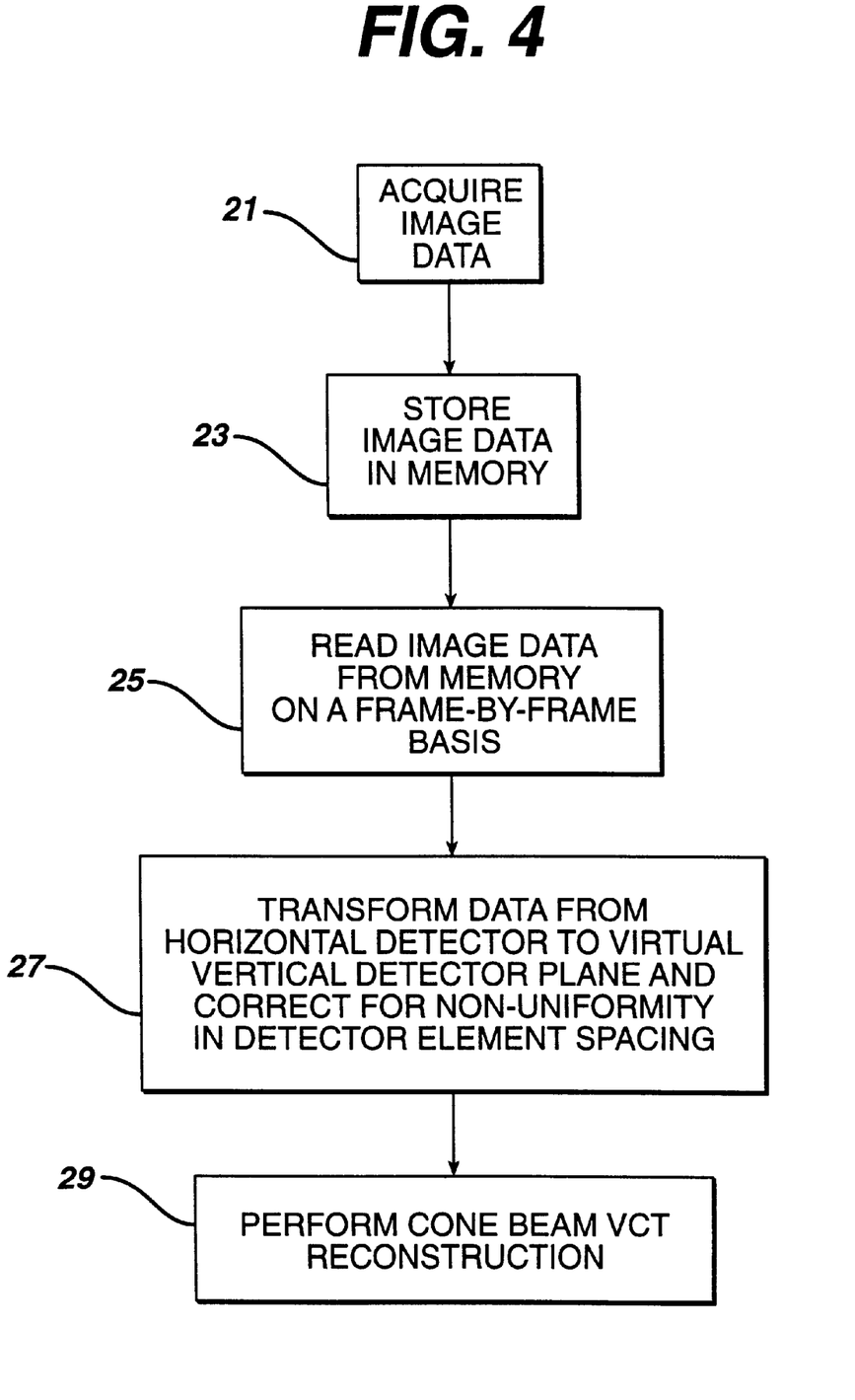
FIGS. 4 and 6 are flow charts illustrating the method of the invention in accordance with embodiments of the invention for reconstructing a 3-D representation of an object being imaged by the apparatus shown in FIG. 3.

The method of the invention in accordance with the preferred embodiment is illustrated by the flow chart of FIG. 4. Block 21 represents the image data acquisition process. Once the image data is acquired, the image data is stored in the system data storage component 12, as represented by block 23. The computer 10 then reads the image data out of the data storage component 12 on a frame-by-frame basis, as indicated by block 25. As the data is read out of the data storage component 12, the computer 10 transforms the data into a form suitable for cone beam VCT reconstruction, as indicated by block 27.

During the transformation process represented by block 27, the data is transformed from the horizontal detector plane of the circular tomosynthesis geometry into data in a virtual vertical detector plane of the cone beam VCT geometry. During this transformation process, the data is also corrected for non-uniformity in detector element spacing in the vertical detector plane. The computer 10 then performs cone beam VCT reconstruction, as indicated by block 29. The step of transforming the data and of correcting the transformed data for non-uniformity in detector element spacing in the virtual vertical detector plane will be described below in detail with respect to FIG. 5.

Cone beam VCT reconstruction is well known in the industry. One well known algorithm for performing cone beam reconstruction is the Feldkamp cone-beam reconstruction algorithm. Other types of algorithms including modifications of the Feldkamp algorithm with filtering and back-projection code segments, are also known in the art that are suitable for performing cone beam VCT reconstruction represented by block 29 in FIG. 4. The Feldkamp algorithm is disclosed in an article entitled "Practical Cone-Beam Algorithm," by L. Feldkamp, L. Davis and J. Kress, J. Opt. Soc. Am., A/Vol. 1, No. 6, June 1984.

This algorithm is also disclosed in a text book entitled "Principles of Computerized Tomographic Imaging", by A. Kak and M. Slaney. It will be understood by those skilled in the art that the invention is not limited to any particular algorithm for performing cone beam VCT reconstruction. Since the Feldkamp algorithm and other VCT reconstruction algorithms are well known in the industry, the manner in which such a VCT reconstruction algorithm is applied to the data collected in accordance with the invention will not be described herein in the interest of brevity. Those skilled in the art will understand how such an algorithm is applied.

Typical cone beam VCT systems utilize an x-ray source which projects a cone of x-rays through the object being imaged. In order to capture these x-rays, the detector in a typical cone beam VCT system is disposed in a plane which is orthogonal to the plane in which a detector in a circular tomosynthesis system is disposed. Cone beam VCT reconstruction algorithms that are currently available are designed to handle data that has been acquired by a detector positioned in this manner. The method of the invention enables data acquired by a circular tomosynthesis detector to be transformed into data which appears to have been collected by a cone beam VCT detector. This transformation process, which includes the process of correcting the transformed data for non-uniformity in detector element spacing in the virtual vertical detector plane, will now be described with reference to FIG. 5.

By way of example and not limitation, the x-ray source 19 is at a particular location $(x,y,z)=(x_0,0,0)$ on the circular trajectory 36. The detector 15 is disposed in a plane which is parallel to the plane in which the source 19 is rotated. The detector 15 is at height $z=z_t$. The detector 15 collects the x-ray transmission intensity data of the scanned object (not shown). The invention transforms the data collected by the horizontal detector 15 into data in a virtual vertical detector plane, which is the plane labeled with the number 35 in FIG. 5. Each row 38 of the horizontal detector 15 is transformed to a row 39 in the virtual vertical detector plane 35. The rows 38 in the horizontal detector 15 and the rows 39 in the virtual vertical detector plane 35 are parallel to the y axis.

Figure 5:
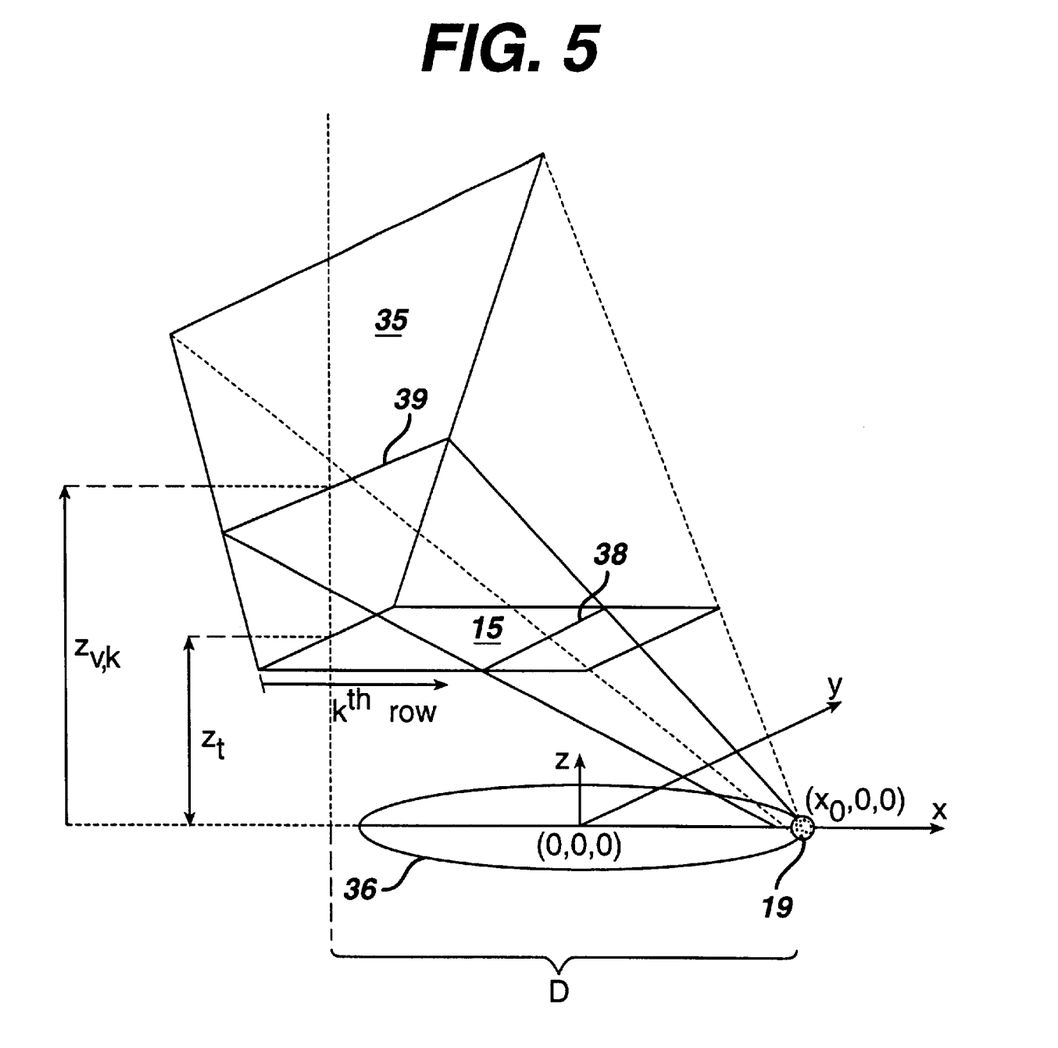
FIG. 5 demonstrates the transformation process performed by the method represented by the flow chart of FIG. 4 to transform data collected by a horizontal detector of a circular tomosynthesis system into data in a virtual vertical detector plane.
Figure 6:
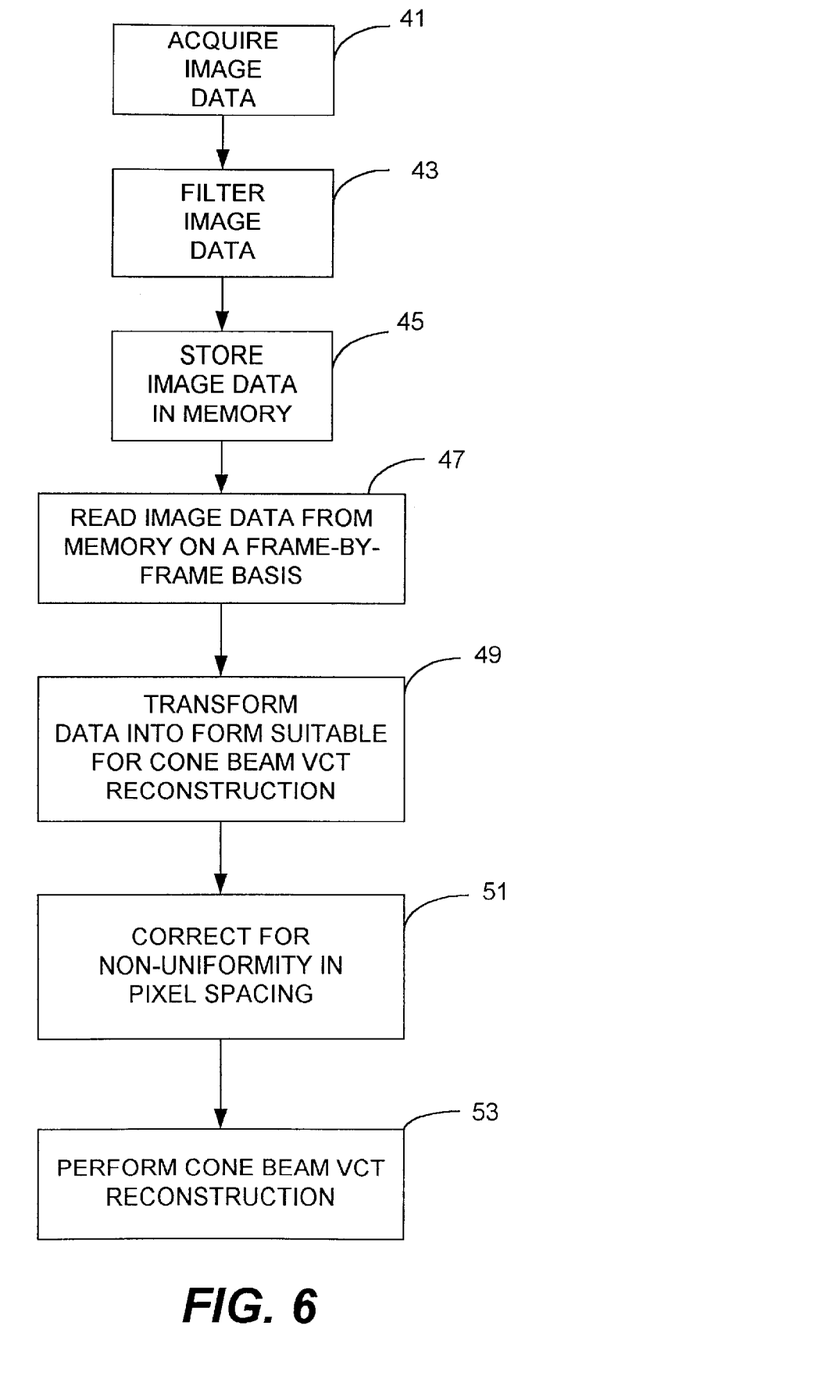

For a horizontal detector 15 having a detector element spacing of $\Delta_t$, the $k^{th}$ row of the horizontal detector 15 is transformed to a row of the virtual vertical detector plane 35 at height $Z_{v,k}$, where $Z_{v,k}$ is defined by the equation:

$$z_{v,k}=z_t D/(D-k\Delta_t), \qquad \text{Equation 1}$$

where D is the distance from the location of the x-ray source 19 to the virtual vertical detector plane 35 along the x axis. The vertical (z direction) spacing, $\Delta_{z,k}$, between the $k^{th}$ and $(k-1)^{th}$ rows on the vertical detector is defined by the equation:

$$\Delta_{z,k}=z_{v,k}-z_{v,k-1} \qquad \text{Equation 2}$$

$$=(z_{v,k}/(D-(k-1)\Delta_t))\cdot\Delta_t \qquad \text{Equation 3}$$

The detector element spacing, $\Delta_{y,k}$, of the row data (in y direction) in the virtual vertical detector plane 35 is defined by the equation:

$$\Delta_{y,k}=(z_{v,k}/z_t)\cdot\Delta_t \qquad \text{Equation 4}$$

It should be noted that the detector element spacing of the horizontal detector 15 in the x and y directions does not have to be equal, as will be understood by those skilled in the art.

Once the data is transformed to the virtual vertical detector plane 35 from the horizontal detector 15 in accordance with these equations, the data is corrected for non-uniformity in detector element spacing in the virtual vertical detector plane 35. Algorithms for cone beam VCT reconstruction can then be used, such as, for example, the Feldkamp algorithm, to reconstruct a 3-D image of the object.

When the data from the horizontal detector 15 is transformed to data in the virtual vertical detector plane 35, the detector element spacing of the virtual vertical detector plane 35 will not be perfectly uniform. VCT reconstruction algorithms currently in use are designed to handle data collected by detectors having a uniform detector element spacing. Therefore, the image data should be processed to compensate for the non-uniformity in detector element spacing before an "off-the-shelf" VCT reconstruction algorithm, such as the Feldkamp algorithm is used to reconstruct the 3-D image.

The computer 10 performs the portion of step 27 directed to correcting for non-uniformity in detector element spacing by drawing a ray from each detector element in the virtual vertical detector plane 35 corresponding to the transformed data through the horizontal detector 15 to the source 19. A determination is then made by the computer 10 as to which detector element in the horizontal detector 15 the ray intersects. The intensity values of the intersected detector element and of a plurality of detector elements surrounding the intersected detector element are then utilized by the computer 10 to interpolate an intensity value to be assigned to the corresponding detector element in the virtual vertical detector plane 35.

The interpolation process can be as simple as averaging the intensity values of the group of detector elements to obtain a mean intensity value, which is then assigned to the corresponding detector element in the virtual vertical detector plane 35. Those skilled in the art will understand that a plurality of different interpolation schemes are suitable for this purpose.

It should be noted that the tasks represented by block 27 in FIG. 4 may be performed by code which is separate from the cone beam VCT reconstruction algorithm. Those skilled in the art will understand the manner in which the code needed to perform the tasks represented by block 27 can be designed. It should also be noted that an existing cone beam VCT reconstruction algorithm can be modified to perform the tasks represented by block 27 in addition to performing the normal cone beam VCT reconstruction task. This is accomplished by modifying the filtering and back-projection portions of the cone beam VCT reconstruction algorithm to take into account the non-uniformity in detector element spacing in the virtual vertical detector plane 35. Those skilled in the art will understand the manner in which an existing cone beam VCT reconstruction algorithm may be modified in this fashion to perform all of these functions.

Those skilled in the art will understand that the invention is not limited to the embodiments discussed above with reference to FIGS. 3–5. Those skilled in the art will understand that modifications can be made to the embodiments discussed above which are within the scope of the invention. It should also be noted that, although the invention has been discussed with reference to imaging a patient, the invention is also applicable to industrial uses, such as, for example, imaging printed circuit boards. Those skilled in the art will understand how the invention may be utilized for such a purpose.

What is claimed is:

1. An apparatus for generating a 3-D image from a plurality of 2-D projection images, the apparatus comprising:
    a circular tomosynthesis system, the system comprising an x-ray source and a detector, the x-ray source projecting x-rays towards an object being imaged, the detector detecting x-rays projected by the x-ray sources, the detector generating electrical signals in response to the x-rays impinging thereon, the electrical signals corresponding to image data acquired by the circular tomosynthesis system; and
    a logic device configured to receive the electrical signals generated by the detector, said logic being configured to transform the circular tomosynthesis image data into cone beam volumetric computed tomography (cone beam VCT) image data.

2. The apparatus of claim 1, wherein said logic device is a computer, said computer being configured to execute a transformation algorithm, the transformation algorithm transforming the circular tomosynthesis image data into cone beam VCT image data, said computer further being configured to execute a cone beam VCT reconstruction algorithm which operates on the transformed image data to generate the 3-D image.

3. The apparatus of claim 2, wherein the detector of the circular tomosynthesis system is disposed in a plane which is parallel with respect to a plane of trajectory of the x-ray source of the circular tomosynthesis system, wherein the transformation algorithm transforms the image data collected by the detector of the circular tomosynthesis system into a virtual vertical detector plane which is orthogonal to the plane in which the tomosynthesis detector is disposed, the virtual vertical detector plane corresponding to a plane in which a detector of a cone beam VCT system would be disposed in relation to an x-ray source of a cone beam VCT system.

4. The apparatus of claim 3, wherein when the image data is transformed to the virtual vertical detector plane, a $k^{th}$ row of the detector of the circular tomosynthesis system is transformed to a row of the virtual vertical detector plane at a vertical height $z_{v,k}$ along a Z axis, where $z_{v,k}$ is defined by an equation:

$$z_{v,k} = z_t D/(D - k\Delta_t),$$

wherein $z_t$ corresponds to a vertical height along the Z axis of the plane in which the detector of the circular tomosynthesis system is disposed, wherein D is the distance from the location of the x-ray source of the circular tomosynthesis system to the virtual vertical detector plane along an X axis, the X axis being orthogonal to the Z axis, and wherein $\Delta_t$ corresponds to a detector element spacing of the detector elements of the circular tomosynthesis system detector, and wherein the vertical spacing along the Z axis, $\Delta_{z,k}$, between the $k^{th}$ and $(k-1)^{th}$ rows of the image data in the virtual vertical detector plane is defined by:

$$\Delta_{z,k} = z_{v,k} - z_{v,k-1}$$
$$= (z_{v,k}/(D - (k-1)\Delta_t)) \cdot \Delta_t,$$

and wherein the detector element spacing, $\Delta_{y,k}$, of the image data in the virtual vertical detector plane along the Y axis is defined by an equation:

$$\Delta_{y,k} = (z_{v,k}/z_t) \cdot \Delta_t.$$

5. The apparatus of claim 4, wherein once the image data has been transformed to image data in the virtual vertical detector plane, the transformed image data is processed by the computer to correct for any non-uniformity in detector element spacing in the direction along the Y and Z axes of the detector elements of the virtual vertical detector plane.

6. The apparatus of claim 5, wherein the computer processes the transformed image data to correct for any non-uniformity in detector element spacing by executing a correction algorithm which performs the steps of:
    drawing a ray from each detector element of the virtual vertical detector plane corresponding to the transformed image data through the detector of the circular tomosynthesis system to the x-ray source of the circular tomosynthesis system;
    determining which detector element in the detector of the circular tomosynthesis system the ray intersects; and
    utilizing the intensity values of the intersected detector element and of a plurality of detector elements surrounding the intersected detector element in the detector of the circular tomosynthesis system to interpolate an intensity value to be assigned to each corresponding detector element in the virtual vertical detector plane.

7. The apparatus of claim 6, wherein the correction algorithm interpolates an intensity value by utilizing the intensity values of the intersected detector element and of the plurality of detector elements surrounding the intersected detector element to obtain an average intensity value which is assigned to the corresponding detector element in the virtual vertical detector plane.

8. The apparatus of claim 7, wherein the correction algorithm is comprised by the cone beam VCT reconstruction algorithm.

9. The apparatus of claim 7, wherein the cone beam VCT reconstruction algorithm is a Feldkamp algorithm.

10. The apparatus of claim 8, wherein the correction algorithm is comprised by the cone beam VCT reconstruction algorithm, wherein the cone beam VCT reconstruction algorithm is a modified Feldkamp algorithm, the modified Feldkamp algorithm comprising filtering and back-projection code segments which have been modified to perform functionalities of the correction algorithm.

11. A method for generating a 3-D image from a plurality of 2-D projection images, the method comprising the steps of:
    utilizing a circular tomosynthesis system to acquire the 2-D projection images, the system comprising an x-ray source and a detector, the x-ray source projecting x-rays through an object being imaged, the detector detecting x-rays which pass through the object, the detector generating electrical signals in response to the x-rays impinging thereon, the electrical signals corresponding to image data acquired by the circular tomosynthesis system; and
    transforming the circular tomosynthesis image data into cone beam volumetric computed tomography (cone beam VCT) image data; and performing cone beam VCT reconstruction on the transformed image data to generate the 3-D image.

12. The method of claim 11, wherein the detector of the circular tomosynthesis system is disposed in a plane which is parallel with respect to a plane of trajectory of the x-ray source, wherein the transformation step transforms the image data collected in the plane in which the detector of the circular tomosynthesis system is disposed into a virtual vertical detector plane which is orthogonal to the plane of trajectory of the x-ray source, the virtual vertical detector plane corresponding to a plane in which a detector of a cone beam VCT system would be disposed in relation to an x-ray source of a cone beam VCT system.

13. The method of claim 12, wherein during the transformation step, a $k^{th}$ row of the detector of the circular tomosynthesis system is transformed to a row of the virtual vertical detector plane at a vertical height $z_{v,k}$ along a Z axis, where $z_{v,k}$ is defined by an equation:

$$z_{v,k} = z_t D/(D - k\Delta_t),$$

wherein $z_t$ corresponds to a vertical height along the Z axis of the plane in which the detector of the circular tomosynthesis system is disposed, wherein D is the distance from the location of the x-ray source of the circular tomosynthesis system to the virtual vertical detector plane along an X axis, the X axis being orthogonal to the Z axis, and wherein $\Delta_t$ corresponds to a detector element spacing of the detector elements of the detector of the circular tomosynthesis system, and wherein the vertical spacing along the Z axis, $\Delta_{z,k}$, between the $k^{th}$ and $(k-1)^{th}$ rows of the image data in the virtual vertical detector plane is defined by:

$$\Delta_{z,k} = z_{v,k} - z_{v,k-1}$$
$$= (z_{v,k} / (D - (k-1)\Delta_t)) \cdot \Delta_t,$$

and wherein the detector element spacing, $\Delta_{y,k}$, of the image data in the virtual vertical detector plane along the Y axis is defined by an equation:

$$\Delta_{y,k} = (z_{v,k}/z_t) \cdot \Delta_t.$$

14. The method of claim 13, wherein after the step of transforming the image data and before the step of performing cone beam VCT reconstruction, a correction step is performed on the transformed image data, the correction step processing the transformed image data to correct for any non-uniformity in detector element spacing in the direction along the Y and Z axes of the detector elements of the virtual vertical detector plane.

15. The method of claim 14, wherein the correction step corrects for any non-uniformity in detector element spacing by performing the steps of:

drawing a ray from each detector element of the virtual vertical detector plane corresponding to the transformed image data through the detector of the circular tomosynthesis system to the x-ray source of the circular tomosynthesis system;

determining which detector element in the detector of the circular tomosynthesis system the ray intersects; and utilizing the intensity values of the intersected detector element and of a plurality of detector elements surrounding the intersected detector element in the detector of the circular tomosynthesis system to interpolate an intensity value to be assigned to each corresponding detector element in the virtual vertical detector plane.

16. The method of claim 15, wherein during the step of utilizing the intensity values, the intensity value to be assigned is interpolated by utilizing the intensity values of the intersected detector element and of the plurality of detector elements surrounding the intersected detector element to obtain an average intensity value to be assigned to the corresponding detector element in the virtual vertical detector plane.

17. The method of claim 16, wherein the method is performed by a computer, the computer being configured to execute a transformation algorithm, the transformation algorithm transforming the circular tomosynthesis image data into cone beam volumetric computed tomography image data, said computer being configured to execute a cone beam volumetric computed tomography (VCT) reconstruction algorithm which operates on the transformed image data to generate the 3-D image.

18. The method of claim 17, wherein the correction step is performed during the step of performing cone beam VCT reconstruction.

19. The method of claim 17, wherein the cone beam VCT reconstruction step is performed by a cone beam VCT reconstruction algorithm.

20. The method of claim 19, wherein the cone beam VCT reconstruction algorithm is a Feldkamp algorithm.

21. The method of claim 19, wherein the cone beam VCT reconstruction algorithm is a modified Feldkamp algorithm, the modified Feldkamp algorithm comprising filtering and back-projection code segments which have been modified to perform functionalities of the correction step.

22. A computer program for generating a 3-D image from a plurality of 2-D projection images, the 2-D projection images being acquired by a circular tomosynthesis system, the system comprising an x-ray source and a detector, the x-ray source projecting x-rays through an object being imaged, the detector detecting x-rays which pass through the object, the detector generating electrical signals in response to the x-rays impinging thereon, the electrical signals corresponding to image data acquired by the circular tomosynthesis system, the computer program being embodied on a computer-readable medium, the program comprising:

a first code segment, the first code segment transforming the circular tomosynthesis image data into cone beam volumetric computed tomography (cone beam VCT) image data; and a second code segment, the second code segment performing cone beam VCT reconstruction on the transformed image data to generate the 3-D image.

23. The program of claim 22, wherein the detector of the circular tomosynthesis system is disposed in a plane which is parallel with respect to a plane of trajectory of the x-ray source, wherein the first code segment transforms the image data collected in the plane of the detector of the circular tomosynthesis system into a virtual vertical detector plane which is orthogonal to the plane of trajectory of the X-ray source, the virtual vertical detector plane corresponding to a plane in which a detector of a cone beam VCT system would be disposed in relation to an x-ray source of a cone beam VCT system.

24. The program of claim 23, wherein the first code segment transforms a $k^{th}$ row of the detector of the circular tomosynthesis system to a row of the virtual vertical detector plane at a vertical height $z_{v,k}$ along a Z axis, where $z_{v,k}$ is defined by an equation:

$$z_{v,k} = z_t D/(D - k\Delta_t),$$

wherein $z_t$ corresponds to a vertical height along the Z axis of the plane in which the detector of the circular tomosynthesis system is disposed, wherein D is the distance from the location of the x-ray source of the circular tomosynthesis system to the virtual vertical detector plane along an X axis, the X axis being orthogonal to the Z axis, and wherein $\Delta_t$ corresponds to a detector element spacing of the detector elements of the detector of the circular tomosynthesis system, and wherein the vertical spacing along the Z axis, $\Delta_{z,k}$, between the $k^{th}$ and $(k-1)^{th}$ rows of the image data in the virtual vertical detector plane is defined by:

$$\Delta_{z,k} = z_{v,k} - z_{v,k-1}$$
$$= (z_{v,k} / (D - (k-1)\Delta_t)) \cdot \Delta_t,$$

and wherein the detector element spacing, $\Delta_{y,k}$, of the image data in the virtual vertical detector plane along the Y axis is defined by an equation:

$$\Delta_{y,k} = (z_{v,k}/z_t) \cdot \Delta_t.$$

25. The program of claim 24, further comprising a third code segment, the third code segment performing a correction operation on the transformed image data, the correction operation processing the transformed image data to correct for any non-uniformity in detector element spacing in the direction along the Y and Z axes of the detector elements of the virtual vertical detector plane.

26. The program of claim 25, wherein the third code segment corrects for any non-uniformity in detector element spacing by:

drawing a ray from each detector element of the virtual vertical detector plane corresponding to the transformed image data through the detector of the circular tomosynthesis system to the x-ray source of the circular tomosynthesis system;

determining which detector element in the detector of the circular tomosynthesis system the ray intersects; and utilizing the intensity values of the intersected detector element and of a plurality of detector elements surrounding the intersected detector element in the detector of the circular tomosynthesis system to interpolate an intensity value to be assigned to each corresponding detector element in the virtual vertical detector plane.

27. The program of claim 26, wherein the third code segment interpolates the intensity value to be assigned by utilizing the intensity values of the intersected detector element and of the plurality of detector elements surrounding the intersected detector element to obtain an average intensity value to be assigned to the corresponding detector element in the virtual vertical detector plane.

* * * * *